United States Patent [19]

Egner et al.

[11] Patent Number: 5,003,262

[45] Date of Patent: Mar. 26, 1991

[54] EDDY CURRENT SYSTEM WITH INTERFERENCE SIGNAL REJECTION

[75] Inventors: Harald Egner, Stuttgart; Robert Russ, Pforzheim, both of Fed. Rep. of Germany; Paul Anthonio, Amsterdam, Netherlands

[73] Assignee: Fraunhofer-Gesellschaft zur Forderung der angewandten Forschung e.V., Fed. Rep. of Germany

[21] Appl. No.: 356,347

[22] Filed: May 24, 1989

[30] Foreign Application Priority Data

May 24, 1988 [DE] Fed. Rep. of Germany ....... 3817574

[51] Int. Cl.$^5$ ............................................. G01N 27/90
[52] U.S. Cl. ..................................... 324/233; 324/234; 324/202; 324/225
[58] Field of Search ................................. 324/233–243

[56] References Cited

U.S. PATENT DOCUMENTS

| 3,895,290 | 7/1975 | Audenard et al. | 324/233 |
| 3,904,957 | 1/1975 | Griese | 324/233 |
| 4,128,803 | 12/1978 | Payne | 324/233 X |
| 4,331,920 | 5/1982 | Kalisch et al. | 324/233 X |
| 4,486,713 | 12/1984 | Gifford | 324/233 X |
| 4,514,692 | 4/1985 | Johnson et al. | 324/233 X |
| 4,603,295 | 7/1986 | Heemstra | 324/233 X |
| 4,628,260 | 12/1986 | Kimoto et al. | 324/233 X |
| 4,700,139 | 10/1987 | Podhrasky | 324/233 X |
| 4,783,630 | 11/1988 | Shoemaker | 324/233 X |
| 4,799,011 | 1/1987 | Muller | 324/237 X |

Primary Examiner—Gerard R. Strecker
Assistant Examiner—Warren S. Edmonds
Attorney, Agent, or Firm—Evenson, Wands, Edwards, Lenahan & McKeown

[57] ABSTRACT

An eddy current sensor having a coil set with a reference coil and a measuring coil, and a sine generator whose output signal is applied to the reference coil and the measuring coil. The output signals of these coils are subtracted from one another by a first subtracter, whose ouput signal is applied to a first modulator and to a second demodulator through a 90 degree phase shifter. The output signal of the sine generator is provided to the first and second demodulators as an additional signal via a phase shifter having an adjustable phase angle. A phase angle is selected such that the interference signals have a specified direction in the formed signal plane. The output signal from the first demodulator is applied through an amplifier having an adjustable amplifying factor (a) to an input of a second subtracter. Similarly, the output signal of the second demodulator is provided through an amplifier having an adjustable amplifying factor (b) to the second subtracter. The second subtracter output provides an output signal from which a trigger threshold can be formed and an object to be identified measured.

14 Claims, 4 Drawing Sheets

EDDY CURRENT SYSTEM WITH INTERFERENCE SIGNAL REJECTION

BACKGROUND AND SUMMARY OF THE INVENTION

The present invention relates to an eddy current sensor having a measuring coil forming a magnetic field in which an object to be identified is insertable.

Eddy current sensors, which by way of illustration are utilized in non-destructive testing are known, for example, from the book "Magnetische und magnetinduktive Werkstoffprüfung" by H. Heppner and H. Stroppe, VEB Deutscher Verlag fur Grundstoffindustrie, Leipzig, 2. Auflage, 1969 or from the article "Elektronik in der zerstörungsfreien Werkstoffprüfung" by H. Luz, published in "Der Elektroniker", 1974, issue 9, pages 9 to 11.

The state of the art eddy current sensors are usually provided with a measuring coil, in the magnetic field of which the object to be identified is arranged, as well as with a reference coil. Furthermore, a signal generator, by way of illustration a sine generator, is provided, the output signal of which is applied to the coils. The output signals applied to the two coils are subtracted from each other by means of a subtracter. The output signal from the subtracter is directly applied to the first demodulator and via a 90° phase shifter to a second demodulator, whereby the output signal from the sine generator, which is shifted via a phase shifter with an adjustable phase angle, is applied to the demodulators as an additional signal.

Due to the twofold demodulation, the (amplified) sensor signal is present as a vector in the "complex impedance plane", whereby the magnitude and the phase of the signal may be drawn upon for evaluation.

As, furthermore, the signal from the sine generator is phase shifted by $0° \leq \gamma \leq 360°$ ($\gamma$ describing the angle about which the axes of the signal plane formed are turned compared to the axes of the impedance plane), in a parallel branch by means of an adjustable phase angle, the desired signal, e.g. the signal of a welded seam, and the interference signal, which by way of illustration may be produced by lifting effects of one or both coils, can lie in any angle $\alpha$ to one another, the interference signal usually being substantially greater in magnitude than the desired signal.

Customarily, the complex signal is displayed on a screen and visually assessed. In order to be able to identify the interesting signal (desired signal), the angle $\gamma$ at the phase shifter is set in such a manner that the interference signal comes to lie exactly in the direction of the y axis. "Channel X" is subsequently drawn upon for evaluation, e.g. by means of an "intuitively" set trigger threshold.

The state of the art sensors utilized, by way of illustration, for material testing have a number of disadvantages.

First of all, it should be understood that a visual assessment on a screen is not suitable if the sensor is to be integrated in automated equipment for testing material.

Moreover, in the known sensors only the projection of the desired signal on the x axis is evaluated. In this manner the signal-to-interference ratio to the interference signal and to noise is further reduced.

Moreover, the angle $\gamma$ has to be precisely adjusted in known sensors. Minimal changes in the properties of the object to be tested-such as occur, by way of illustration, when changing the batch-may result in incorrect identification.

An object of the present invention is to provide an eddy current sensor, which, by way of illustration, can be utilized for material testing, permitting automated evaluation of the signal at full signal-to-interference ratio.

A solution to the aforegoing object in accordance with the present invention and its further embodiments is set forth in the claims hereto.

Other objects, advantages and novel features of the present invention will become apparent from the following detailed description of the invention when considered in conjunction with the accompanying drawings.

DETAILED DESCRIPTION OF THE DRAWINGS

Figure 1:
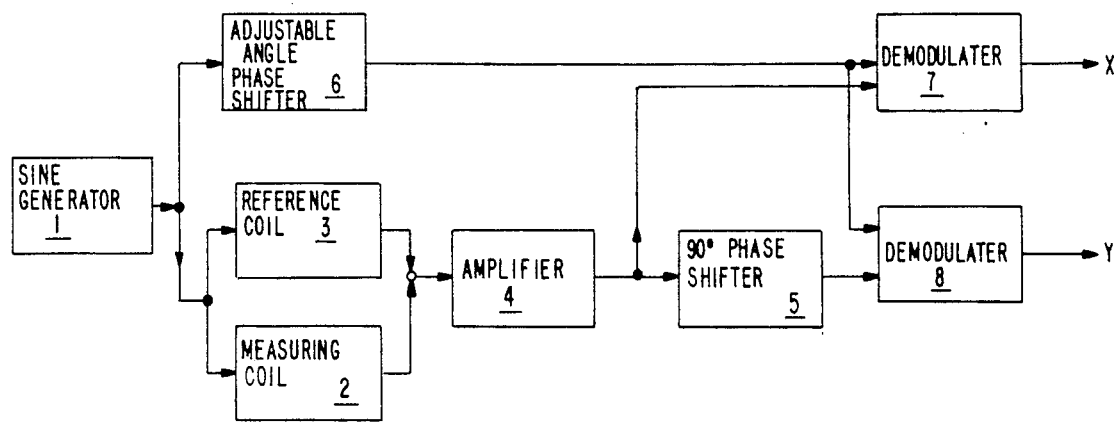
FIG. 1 is a block diagram of a state of the art eddy current sensor, on which the present invention is based.

FIG. 1 depicts a conventional eddy current sensor provided with a sine generator 1 as a signal generator, the output signal of which is applied to a measuring coil 2, to a reference coil 3 and to the input connection of phase shifter 6 having an adjustable phase angle ranging between 0° and 360°.

The output signals from the measuring coil 2 and from the reference coil 3 are first subtracted from one another (reference marks 2-3) and amplified by means of an amplifier 4. The output signal from amplifier 4 is applied to an input connection of demodulator 8 via a phase shifter 5 having a stationary phase angle of 90°. Furthermore, the output signal from amplifier 4 is directly applied to the input connection of demodulator 7. The output signal of phase shifter 6 having an adjustable phase angle is applied to the other input connections of demodulators 7 and 8.

The output signals of the demodulators 7 and 8 are designated x channel and y channel in keeping with the literature in the field.

Figure 2:
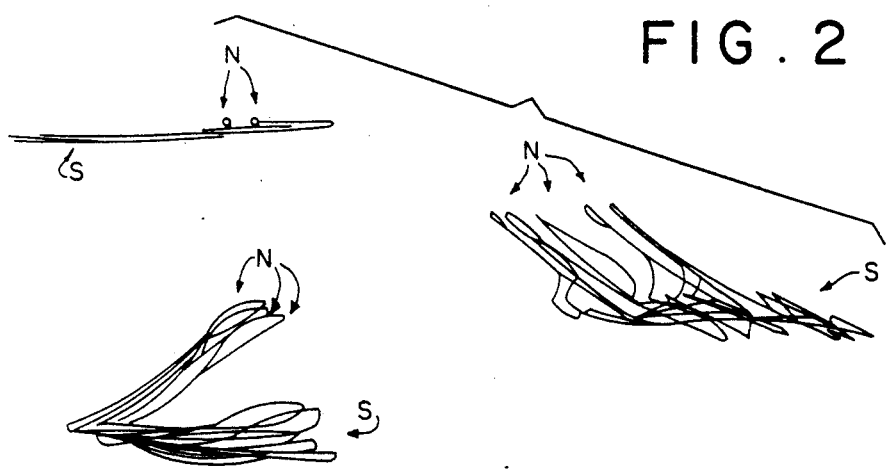
FIG. 2 shows schematic views of examples of sensor signals in the "impedance plane"

FIG. 2 shows examples of sensor signals (x and y channel) in the so-called "complex impedance plane", whereby N designates the desired signal and S the interference signal.

As is quite evident from the illustrated examples, the relationship of the magnitude of the two signals differs "depending on the turn" of the individual signals: by way of illustration, the desired signal may be much smaller than the interference signal (upper left section of FIG. 2), the same size (lower left section of FIG. 2) or the interference signal may be substantially smaller than the desired signal (right section of FIG. 2).

Figure 3:
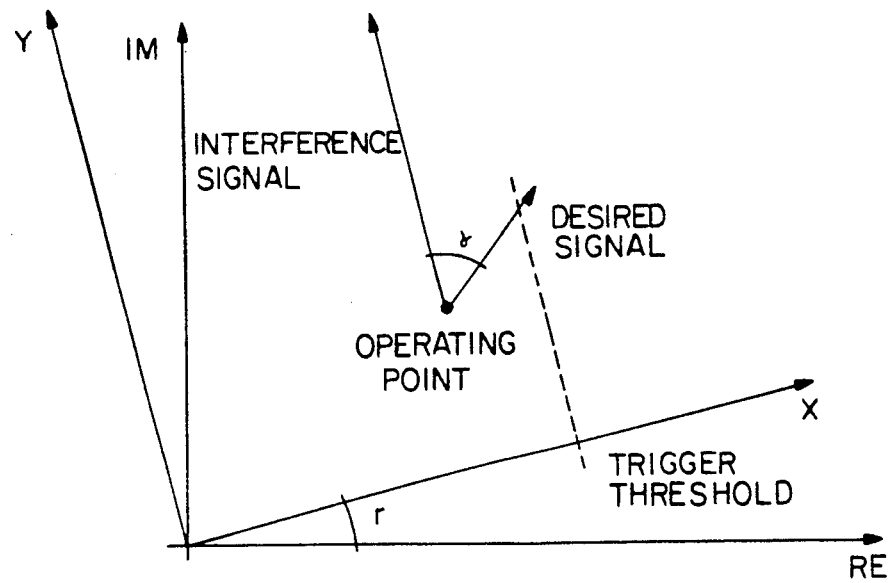
FIG. 3 is a graph depicting signal evaluation of conventional eddy current sensors.
Figure 4:
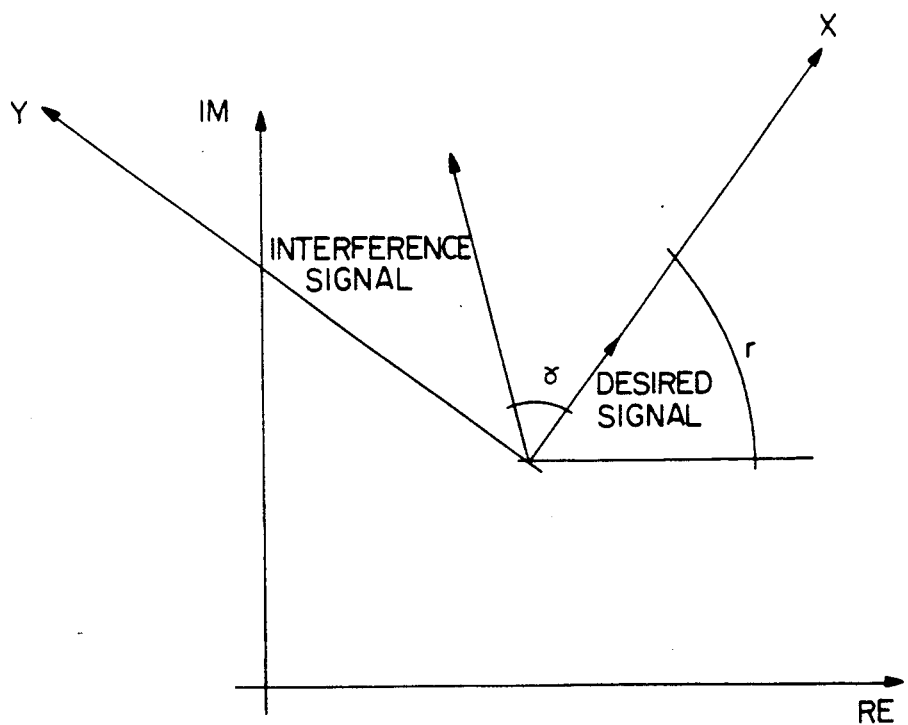
FIG. 4 is a graph depicting the signal evaluation utilizing an eddy current sensor arrangement constructed according to a preferred embodiment of the invention.

In the case of conventional eddy current sensors, signal evaluation occurs in the manner illustrated in FIG. 3:

As previously explained, the sensor differential signal lies as a vector in the complex plane due to the two fold demodulation in demodulators 7 and 8, $\gamma$ being the angle about which the x and y axis are turned compared to the axes RE and IM of the impedance plane by means of phase shifting about angle $\gamma$ by phase shifter 6. Angle $\gamma$ is set at a phase shifter 6 in such a manner that the interference signal comes to lie exactly in the direction of the y axis. Channel X, i.e. the output signal from demodulator 7, is subsequently drawn upon for evaluation via a trigger threshold.

The preceding description distinctly illustrates once more the disadvantage of the state of the art eddy current sensors as already presented in the introduction hereto, namely the deterioration of the signal-to-interference ratio due to the fact that only the projection of the desired signal on the x axis is drawn upon for evaluation.

In order to improve the signal-to-interference ratio, the present invention proceeds from the fundamental concept of drawing upon not only channel X with the projected desired signal for evaluation, but also upon both channels, i.e. the output signals of demodulators 7 and 8.

For this purpose, the xy planed is turned in such a manner that the desired signal comes to lie in the direction of the x axis. In accordance with the present invention, the zero point of the xy coordination system no longer lies in the zero point of the "complex impedance plane", but is shifted in such a way that it comes to lie in the actuating point of the sensor.

For this purpose, the interference signal is suppressed by means of a filter, which couples the X and Y signals:

$$c*Z = a*X - b*Y \text{ with } \tan \alpha = a/b$$

The aforementioned filter suppresses all signals lying in an angle to the x axis. Factor c only describes an adaption of the amplitude of the coupled signals to the following evaluation circuit, by way of illustration to the operation area of an A/D converter.

Figure 5A:
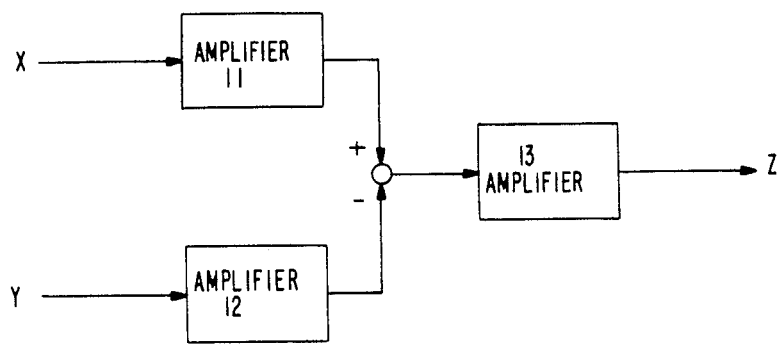
FIGS. 5a and 5b are block diagrams of preferred embodiments of the invention, with which the signal evaluation illustrated in FIG. 4 can be realized, and FIG. 6 schematically depicts self-calibration utilizing preferred embodiments of the invention.

FIG. 5a depicts a preferred embodiment of the invention with fundamental circuit as an expansion of the basic circuit of the eddy current sensor illustrated in FIG. 1.

The signals, i.e. the "x channel and the y channel signal', coming from the output connections of demodulators 7 and 8 (of FIG. 1) are initially amplified in amplifiers 11 and 12 and subsequently subtracted from one another in a subtractor 11-12. The output signal of subtractor 11-12 is amplified by an amplifier 13 and evaluated (z channel).

The angle of the aforedescribed signal supression can be adjusted to an angle $\alpha$ between the desired and interference signal by means of the amplifying factors a and b of the amplifiers 11 and 12.

Figure 5B:
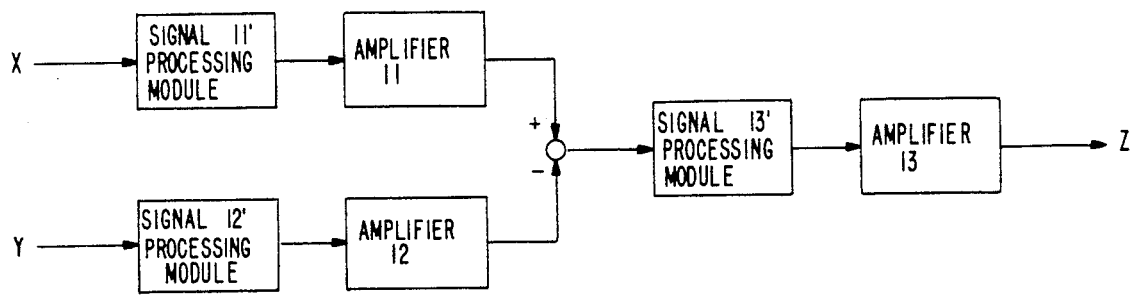

FIG. 5b shows an expanded block diagram of a further embodiment of the invention, as an expansion of the eddy current sensor illustrated in FIG. 1. In this further embodiment, additional signal processing modules 11', 12' and 13', which, by way of illustration, have a high-pass function, a low-pass function, a differentiating or an integrating function, are connected in series ahead of amplifiers 11, 12, and 13.

An automated evaluation of the eddy current sensor output signal having a high signal-interference ratio can be attained by means of the exemplary further improvements over the state of the art eddy current sensors as illustrated in FIGS. 5a and b.

In particular, the evaluation according to the present invention has the striking advantage that, for similar work pieces, the angle $\alpha$ is practically independent of the batch. This means that the magnitude tan $\alpha$, i.e. the ratio of the amplifying factos a/b of amplifiers 11 and 12, can be set once prior to launching an automated test and does not have to be altered during the test even when the batch is changed.

With automated identification of axial features of axially symmetrical work pieces, e.g. of welding seams of longitudinally welded pipes by means of electromagnetic measuring processes, i.e. by means of eddy current or stray flux leakage measurement, there arises the added problem that the electromagnetic properties of the material of a work piece differ from work piece to work piece. Thus, a simple trigger threshold in z channel in FIGS. 5a and b is too unreliable for automated identification of features, as the threshold has to be continuously adjusted to the different work pieces, by way of illustration in the case of batch and/or production changes.

For this reason, a further element of the present invention is that self-calibration, which can be realized hardware and/or software-wise subsequent to digitalization of the sensor signal in a digital-function unit following the z output connection, is provided for orienting axial features.

Figure 6:
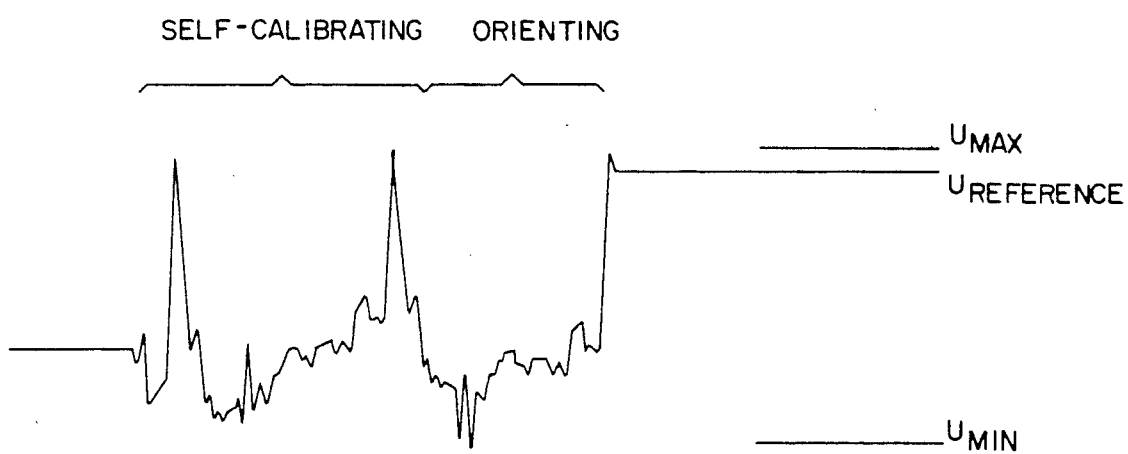

This surveying self-calibration is made more apparent in the following section with reference to FIG. 6:

In the first phase, which may also be called the self-calibration phase, the axially symmetrical work piece is turned approximately 400° and the voltage maximum and minimum occurring during this period are stored. The axial feature to be identified is travelled over at least once during this time. The voltage maximum represents the signal of the sought feature. The two voltage values are joined via the ratio $$U_{reference} u_{max} - (u_{max} - u_{min})*d.$$

During the second phase (orientation), the axially symmetrical work place is turned further until the signal has reached the reference voltage $U_{reference}$ again. In this manner, the axial feature is oriented relative to the sensor.

Factor d constitutes a safety margin and takes the measurement uncertainties caused by mechanical, thermal or electric inaccuracies of the measurement setup into account. At a value of d of 0.05, when the same feature has been maximally scanned three times consecutively, 5% of the total amplitude of the sensors signal is permissible scattering of the amplitude of the feature.

In the aforegoing the present invention has been described by way of illustration without the intention of limiting the scope of the overall inventive concept and/or range of application. The invention set forth in claim 1 hereto may, in particular, find application in automatic identification of eddy current signals with a trigger threshold, the arrangement of the present invention described in claim 10 hereto permitting orienting axial features of axially symmetrical work pieces, e.g. welded seams of longitudinally welded pipes and/or minimum wall strengths of pipes having hexagonal interiors, in an advantageous manner.

However, the embodiment of the present invention set forth in claim 8 hereto may also be utilized in measuring processes other than eddy current measuring processes, by way of illustration, in orienting apparatuses working with stray flux leakage processes (by way of example while employing sensors).

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. An eddy current sensor comprising:
    a coil set having at least one reference coil having an input and an output and at least one measuring coil having an input and an output;
    a sine generator having an output coupled to the reference coil input and the measuring coil input;
    a first subtractor having two inputs and an output, the two inputs of the first subtractor being coupled to the reference coil output and the measuring coil output;
    a first demodulator having two inputs and an output, one first demodulator input being coupled to the first subtractor output;
    a 90° phase shifter having an input and an output, the 90° phase shifter input being coupled to the first subtractor output;
    a second demodulator having two inputs and an output, one second demodulator input being coupled to the 90° phase shifter output;
    an adjustable phase angle phase shifter having an input and an output, the adjustable phase angle phase shifter input being coupled to the sine generator output, and the adjustable phase angle phase shifter output being coupled to the other first demodulator input and the other second demodulator input, the phase angle being adjustable such that interference signals have a specified direction in a formed signal plane;
    a first amplifier having an input and an output and an adjustable amplifying factor (a), the first amplifier input being coupled to the first demodulator output;
    a second amplifier having an input and an output and an adjustable amplifying factor (b), the second amplifier input being coupled to the second demodulator output; and
    a second subtractor having two inputs and an output, one second subtractor input being coupled to the first amplifier output, the other second subtractor input being coupled to the second amplifier output, the second subtractor output providing an output signal ($U_{trig}$) from which a trigger threshold can be formed and an object to be identified is measured.

2. A sensor according to claim 1, wherein said phase angle is adjustable such that a desired signal lies in the direction of an axis of said formed signal plane.

3. A sensor according to claim 1, wherein said adjustable amplifying factors a and b are adjusted prior to testing a batch of objects such that the relationship between the prescribed angle α between desired and interference signals and said factors a and b is:

$$\frac{a}{b} = \tan \alpha$$

where α describes the phase angle between desired and interference signals.

4. A sensor according to claim 3, further comprising a third amplifier having an input and an output and an adjustable amplifying factor (c), said third amplifier input being coupled to the second subtractor output.

5. A sensor according to claim 4, further comprising first, second and third signal processing modules, the first signal processing module being coupled between the first demodulator and the first amplifier, the second signal processing module being coupled between the second demodulator and the second amplifier, and the third signal processing module being coupled between the second subtractor and the third amplifier.

6. A sensor according to claim 5, wherein said first and second signal processing modules have one of a high-pass, low-pass, differentiating and integrating functions.

7. A sensor according to claim 6, wherein, in order to identify axial features in otherwise axially symmetrical work pieces, the work piece is first turned more than 360° and, in order to position said feature over the measuring coil, the work piece is subsequently turned in such a manner that said output signal $U_{trig}$ of said third subtractor attains a value of $$U_{max} - (U_{max} - U_{min})^{*d}$$

with d being in the range of 0.01 ... 0.25.

8. A sensor according to claim 5, wherein, in order to identify axial features in otherwise axially symmetrical work pieces, the work piece is first turned more than 360° and, in order to position said feature over the measuring coil, the work piece is subsequently turned in such a manner that said output signal $U_{trig}$ of said third subtractor attains a value of $$U_{max} - (U_{max} - U_{min})^{*d}$$

with d being in the range of 0.01 ... 0.25.

9. A sensor according to claim 3, wherein, in order to identify axial features in otherwise axially symmetrical work pieces, the work piece is first turned more than 360° and, in order to position said feature over the measuring coil, the work piece is subsequently turned in such a manner that said output signal $U_{trig}$ of said third subtractor attains a value of $$U_{max} - (U_{max} - U_{min})^{*d}$$

with d being in the range of 0.01 ... 0.25

10. A sensor according to claim 1, wherein, in order to identify axial features in otherwise axially symmetrical work pieces, the work piece is first turned more than 360° and, in order to position said feature over the measuring coil, the work piece is subsequently turned in such a manner that said output signal $U_{trig}$ of said third subtractor attains a value of $$U_{max} - (U_{max} - U_{min})^{*d}$$

with d being in the range of 0.01 ... 0.25.

11. A sensor according to claim 1, further comprising a third amplifier having an input and an output and an adjustable amplifying factor (c), said third amplifier input being coupled to the second subtractor output.

12. A sensor according to claim 11, wherein, in order to identify axial features in otherwise axially symmetrical work pieces, the work piece is first turned more than 360° and, in order to position said feature over the measuring coil, the work piece is subsequently turned in such a manner that said output signal $U_{trig}$ of said third contractor attains a value of $$U_{max}-(U_{max}-U_{min})*d$$

with d being in the range of 0.01 ... 0.25

13. A sensor according to claim 1, further comprising first and second signal processing modules, the first signal processing module being coupled between the first demodulator and the first amplifier, and the second signal processing module being coupled between the second demodulator and the second amplifier.

14. A sensor according to claim 13, wherein said first and second signal processing modules have one of a high-pass, low-pass, differentiating and integrating functions.

* * * * *